US008435490B2

(12) United States Patent
Abraham et al.

(10) Patent No.: US 8,435,490 B2
(45) Date of Patent: May 7, 2013

(54) SMALL PEPTIDES SPECIFICALLY BIND TO COLORECTAL CANCERS

(75) Inventors: John Martin Abraham, Woodbine, MD (US); Stephen J. Meltzer, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 370 days.

(21) Appl. No.: 12/664,302

(22) PCT Filed: Jun. 4, 2008

(86) PCT No.: PCT/US2008/065735
§ 371 (c)(1),
(2), (4) Date: Mar. 11, 2010

(87) PCT Pub. No.: WO2009/002669
PCT Pub. Date: Dec. 31, 2008

(65) Prior Publication Data
US 2010/0183511 A1  Jul. 22, 2010

Related U.S. Application Data

(60) Provisional application No. 60/936,669, filed on Jun. 21, 2007, provisional application No. 61/123,868, filed on Apr. 11, 2008.

(51) Int. Cl.
*A61K 51/00* (2006.01)
*A61M 36/14* (2006.01)

(52) U.S. Cl.
USPC ....... 424/1.69; 424/1.11; 424/1.65; 424/1.81; 424/1.85; 424/1.89

(58) Field of Classification Search ......... 424/1.11, 424/1.65, 1.69, 1.73, 1.81, 9.1, 9.2, 1.85, 424/1.89; 514/1, 1.11; 530/300, 328
See application file for complete search history.

(56) References Cited

U.S. PATENT DOCUMENTS

| | | | |
|---|---|---|---|
| 6,159,443 A * | 12/2000 | Hallahan | 424/1.17 |
| 6,440,386 B1 * | 8/2002 | Leung | 424/1.53 |
| 2002/0032307 A1 | 3/2002 | Tong et al. | |
| 2004/0146954 A1 | 7/2004 | Waldman et al. | |
| 2006/0058228 A1 | 3/2006 | Kelly et al. | |
| 2006/0121553 A1 * | 6/2006 | Sun | 435/23 |

OTHER PUBLICATIONS

Shih et al , Chang Gung Med. J, 2002, vol. 25, pp. 349-354.*
Abdulamir et al, Journal of Experimental & Clinical Cancer Research, 2011, vol. 30, No. 11, pp. 1-13.*
Zhang, H. et al. DOTA-PESIN, a DOTA-Conjugated Bombesin Derivative Designed for the imaging and Targeted Radionuclide Treatment of Bombesin Receptor-Positive Tumor. Eur. J. Nucl. Med. Mol. Imaging. Jan. 30, 2007 (301.01.2007), vol. 34, No. 8, pp. 1198-1208; abstract; fig 6; p. 1201, right col., para 4, 5; p. 1202, left col., para 1; right col; para 3; p. 1204. right col., para 2.
International Search Report dated Dec. 23, 2008.
International Preliminary Report on Patentability for PCT/US2008/065735 mailed on Jan. 7, 2010.

* cited by examiner

*Primary Examiner* — D L Jones
(74) *Attorney, Agent, or Firm* — Banner & Witcoff, Ltd.

(57) ABSTRACT

Cancers are extremely heterogeneous in terms of the frequency and types of mutations present in different malignant tumors. Thus, it is likely that uniform clinical treatment is not optimal for all patients, and that the development of individualized therapeutic regimens may be beneficial. Multiple, unique small peptides bind to cell lines derived from different colon adenocarcinomas. Within two hours of contact, the colorectal cancer cells are able to transfer a $^{32}$P radioisotope from the small peptides to cellular proteins; the transfer occurs at a substantially higher rate than in the colorectal cancer cells than in cell lines derived from other cancers or from normal tissues.

8 Claims, 9 Drawing Sheets

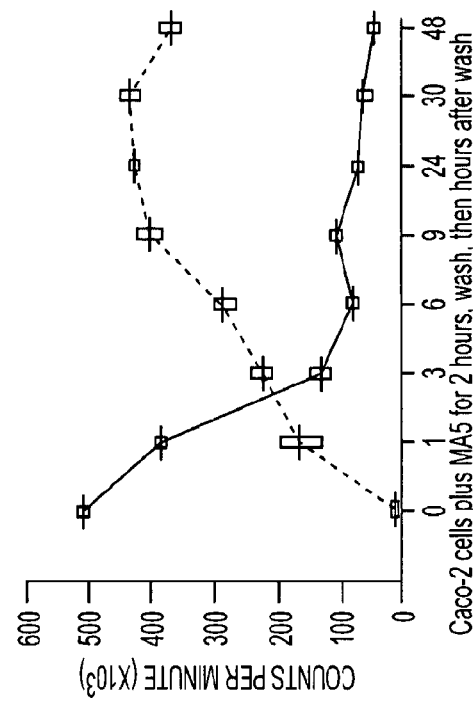
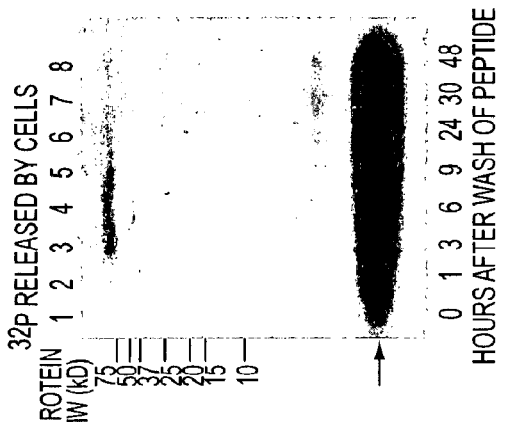
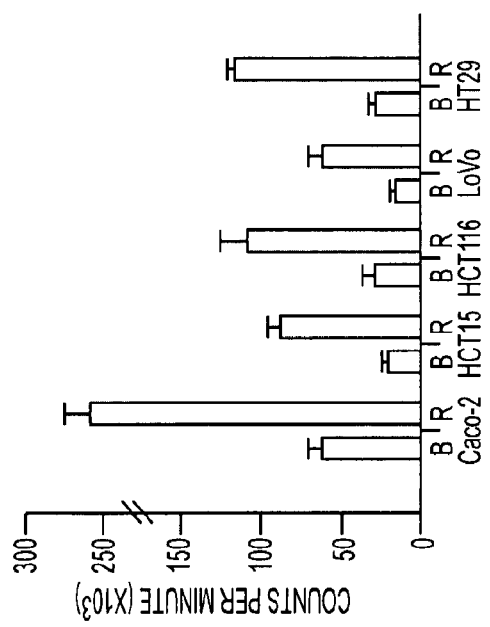

SEQUENCE LISTING

<160> NUMBER OF SEQ ID NOS: 40

<210> SEQ ID NO 1
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 1

Gly Ser Arg Arg Ala Ser Val Gly Ser Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 2

Gly Ser Arg Gly Ala Ser Val Gly Gly Ala
1               5                   10

<210> SEQ ID NO 3
<211> LENGTH: 10

```
<212> TYPE: PRT
<213> ORGANISM: Artificial Sequence
<220> FEATURE:
<223> OTHER INFORMATION: synthetic or recombinant sequence

<400> SEQUENCE: 3

Gly Ser Arg Arg Gly Ser Val Gly Ser Ala
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 4

Gly Ser Arg Arg Gly Ser Val Ala Ser Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 5

Gly Ser Arg Arg Ala Ser Val Ala Ser Ala
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 6

Gly Ser Arg Arg Ala Ser Val Gly Ser Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 7

Gly Ser Arg Gly Gly Ser Val Gly Ser Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 8

Gly Ser Arg Gly Gly Ser Val Ala Ser Ala
1               5                   10

<210> SEQ ID NO 9
<211> LENGTH: 10
<212> TYPE: PRT
<213> ORGANISM: Artificial Sequence
```

```
<220> FEATURE:
<223> OTHER INFORMATION: synthetic or recombinant sequence

<400> SEQUENCE: 9

Gly Ser Arg Gly Gly Ser Val Gly Ser Gly
 1               5                  10

<210> SEQ ID NO 10
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 10

Gly Ser Arg Arg Ala Ser Val Gly Ser Ile Ser Thr Arg Pro Ile His
 1               5                  10                  15

Leu Glu Pro Arg Pro Thr Ala Ala Pro Arg Gly Ser Pro Gly Ile His
            20                  25                  30

Arg Asp

<210> SEQ ID NO 11
<211> LENGTH: 12
<212> TYPE: PRT
<213> ORGANISM: Artificial Sequence
<220> FEATURE:
<223> OTHER INFORMATION: synthetic or recombinant sequence

<400> SEQUENCE: 11

Gly Ser Arg Arg Ala Ser Val Gly Ser Tyr His Val
 1               5                  10

<210> SEQ ID NO 12
<211> LENGTH: 19
<212> TYPE: PRT
<213> ORGANISM: Artificial Sequence
<220> FEATURE:
<223> OTHER INFORMATION: synthetic or recombinant sequence

<400> SEQUENCE: 12

Gly Ser Arg Arg Ala Ser Val Gly Ser Asn Gly Asp Gly Val Phe Ser
 1               5                  10                  15

Leu Val Arg

<210> SEQ ID NO 13
<211> LENGTH: 14
<212> TYPE: PRT
<213> ORGANISM: Artificial Sequence
<220> FEATURE:
<223> OTHER INFORMATION: synthetic or recombinant sequence

<400> SEQUENCE: 13

Gly Ser Arg Arg Ala Ser Val Gly Ser Lys Asn Cys Arg Arg
 1               5                  10

<210> SEQ ID NO 14
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 14

Gly Ser Arg Arg Ala Ser Val Gly Ser Leu Gly Val Leu Arg Leu Val
 1               5                  10                  15
```

```
Pro Ile Val Arg Arg Val Cys Gln Arg Cys Gly Ser Pro Gly Ile His
            20                  25                  30

Arg Asp

<210> SEQ ID NO 15
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 15

Gly Ser Arg Arg Ala Ser Val Gly Ser Val Asp Gly Ala Ser Leu Arg
  1               5                  10                  15

Cys Ser Ala Gln Asp Pro Pro Lys Asp Gly Ser Pro Gly Ile His
            20                  25                  30

Arg Asp

<210> SEQ ID NO 16
<211> LENGTH: 15
<212> TYPE: PRT
<213> ORGANISM: Artificial Sequence
<220> FEATURE:
<223> OTHER INFORMATION: synthetic or recombinant sequence

<400> SEQUENCE: 16

Gly Ser Arg Arg Ala Ser Val Gly Ser Pro Gly Ile His Arg Asp
  1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic or recombinant sequence

<400> SEQUENCE: 17

Gly Ser Arg Arg Ala Ser Val Gly Ser Pro Gly Ile His Arg Asp
  1               5                  10                  15

<210> SEQ ID NO 18
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 18

Gly Ser Arg Arg Ala Ser Val Gly Ser Ala Ala Ala Phe Arg Arg Ala
  1               5                  10                  15

Thr Val Pro Pro Ile Cys Arg Ala Asp Trp Gly Ser Pro Gly Ile His
            20                  25                  30

Arg Asp

<210> SEQ ID NO 19
<211> LENGTH: 9
<212> TYPE: PRT
<213> ORGANISM: Artificial Sequence
<220> FEATURE:
<223> OTHER INFORMATION: synthetic or recombinant sequence

<400> SEQUENCE: 19

Gly Ser Arg Arg Ala Ser Val Gly Ser
  1               5
```

```
<210> SEQ ID NO 20
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 20

Gly Ser Arg Arg Ala Ser Val Gly Ser Arg Val Arg Val Trp His Leu
 1               5                  10                  15

Ser Pro Val Leu Lys Val Ala Gln Leu Leu Gly Ser Pro Gly Ile His
            20                  25                  30

Arg Asp

<210> SEQ ID NO 21
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 21

Gly Ser Arg Arg Ala Ser Val Gly Ser Val Pro Gly Arg Ser Asn Pro
 1               5                  10                  15

Pro Ala Leu Pro Gly Val Tyr Glu Leu Ala Gly Ser Pro Gly Ile His
            20                  25                  30

Arg Asp

<210> SEQ ID NO 22
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 22

Gly Ser Arg Arg Ala Ser Val Gly Ser Val Val Ala Arg Leu Tyr Val
 1               5                  10                  15

Arg Gln Pro Gln Asp Ser Asn Ile Thr Phe Gly Ser Pro Gly Ile His
            20                  25                  30

Arg Asp

<210> SEQ ID NO 23
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 23

Gly Ser Arg Arg Ala Ser Val Gly Ser Asp Ala His Ser Leu Met Ala
 1               5                  10                  15

Gly Pro Thr Ala Glu Ser Leu Glu Phe Leu Gly Ser Pro Gly Ile His
            20                  25                  30

Arg Asp

<210> SEQ ID NO 24
<211> LENGTH: 34
<212> TYPE: PRT
<213> ORGANISM: Artificial Sequence
<220> FEATURE:
<223> OTHER INFORMATION: synthetic or recombinant sequence
```

-continued

```
<400> SEQUENCE: 24

Gly Ser Arg Arg Ala Ser Val Gly Ser Glu Pro Thr Tyr Asn Thr Thr
1               5                   10                  15

Phe Ser Phe Gln Ala Val Asp Tyr Ser Tyr Gly Ser Pro Gly Ile His
            20                  25                  30

Arg Asp

<210> SEQ ID NO 25
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 25

Gly Ser Arg Arg Ala Ser Val Gly Ser Cys Cys Gln Arg Met Gly Trp
1               5                   10                  15

Gly His Phe Arg Leu Thr Val Gly Asn Phe Gly Ser Pro Gly Ile His
            20                  25                  30

Arg Asp

<210> SEQ ID NO 26
<211> LENGTH: 34
<212> TYPE: PRT
<213> ORGANISM: Artificial Sequence
<220> FEATURE:
<223> OTHER INFORMATION: synthetic or recombinant sequence

<400> SEQUENCE: 26

Gly Ser Arg Arg Ala Ser Val Gly Ser Ala Gly Gln Val Thr Ser Ala
1               5                   10                  15

Gly Glu Leu Ser Gly Val Ser His Ile Thr Gly Ser Pro Gly Ile His
            20                  25                  30

Arg Asp

<210> SEQ ID NO 27
<211> LENGTH: 10
<212> TYPE: PRT
<213> ORGANISM: Artificial Sequence
<220> FEATURE:
<223> OTHER INFORMATION: synthetic or recombinant sequence

<400> SEQUENCE: 27

Gly Ser Arg Arg Ala Ser Val Gly Ser Ile
1               5                   10

<210> SEQ ID NO 28
<211> LENGTH: 17
<212> TYPE: PRT
<213> ORGANISM: Artificial Sequence
<220> FEATURE:
<223> OTHER INFORMATION: synthetic or recombinant sequence

<400> SEQUENCE: 28

Gly Ser Arg Arg Ala Ser Val Gly Ser Ile Phe Ser Val Asp Trp Val
1               5                   10                  15

Ala

<210> SEQ ID NO 29
<211> LENGTH: 18
<212> TYPE: PRT
<213> ORGANISM: Artificial Sequence
<220> FEATURE:
```

<223> OTHER INFORMATION: synthetic or recombinant sequence

<400> SEQUENCE: 29

Val Pro Arg Gly Ser Arg Arg Ala Ser Val Gly Ser Pro Gly Ile His
 1               5                  10                  15

Arg Asp

<210> SEQ ID NO 30
<211> LENGTH: 63
<212> TYPE: DNA
<213> ORGANISM: Artificial Sequence
<220> FEATURE:
<223> OTHER INFORMATION: synthetic or recombinant sequence
<221> NAME/KEY: misc_feature
<222> LOCATION: (7)...(57)
<223> OTHER INFORMATION: n = A,T,C or G

<400> SEQUENCE: 30
ggatccnnnn nnnnnnnnnn nnnnnnnnnn nnnnnnnnnn nnnnnnnnnn nnnnnnngga      60
tcc                                                                   63

<210> SEQ ID NO 31
<211> LENGTH: 37
<212> TYPE: PRT
<213> ORGANISM: Artificial Sequence
<220> FEATURE:
<223> OTHER INFORMATION: synthetic or recombinant sequence
<221> NAME/KEY: VARIANT
<222> LOCATION: (13)...(29)
<223> OTHER INFORMATION: Xaa = Any Amino Acid
<221> NAME/KEY: VARIANT
<222> LOCATION: (1)...(37)
<223> OTHER INFORMATION: Xaa = Any Amino Acid
<221> NAME/KEY: VARIANT
<222> LOCATION: (1)...(37)
<223> OTHER INFORMATION: Xaa = Any Amino Acid

<400> SEQUENCE: 31

Val Pro Arg Gly Ser Arg Arg Ala Ser Val Gly Ser Xaa Xaa Xaa Xaa
 1               5                  10                  15

Xaa Xaa Xaa Xaa Xaa Xaa Xaa Xaa Xaa Xaa Xaa Xaa Xaa Gly Ser Pro
            20                  25                  30

Gly Ile His Arg Asp
        35

<210> SEQ ID NO 32
<211> LENGTH: 37
<212> TYPE: PRT
<213> ORGANISM: Artificial Sequence
<220> FEATURE:
<223> OTHER INFORMATION: synthetic or recombinant sequence
<221> NAME/KEY: PHOSPHORYLATION
<222> LOCATION: (5)...(5)
<221> NAME/KEY: VARIANT
<222> LOCATION: (13)...(29)
<223> OTHER INFORMATION: Xaa = Any Amino Acid
<221> NAME/KEY: VARIANT
<222> LOCATION: (1)...(37)
<223> OTHER INFORMATION: Xaa = Any Amino Acid
<221> NAME/KEY: VARIANT
<222> LOCATION: (1)...(37)
<223> OTHER INFORMATION: Xaa = Any Amino Acid

<400> SEQUENCE: 32

Val Pro Arg Gly Ser Arg Arg Ala Ser Val Gly Ser Xaa Xaa Xaa Xaa
 1               5                  10                  15

Xaa Xaa Xaa Xaa Xaa Xaa Xaa Xaa Xaa Xaa Xaa Xaa Xaa Gly Ser Pro
            20                  25                  30

Gly Ile His Arg Asp
        35

<210> SEQ ID NO 33
<211> LENGTH: 34
<212> TYPE: PRT
<213> ORGANISM: Artificial Sequence
<220> FEATURE:
<223> OTHER INFORMATION: synthetic or recombinant sequence
<221> NAME/KEY: PHOSPHORYLATION
<222> LOCATION: (6)...(6)
<221> NAME/KEY: VARIANT
<222> LOCATION: (10)...(26)
<223> OTHER INFORMATION: Xaa = Any Amino Acid
<221> NAME/KEY: VARIANT
<222> LOCATION: (1)...(34)
<223> OTHER INFORMATION: Xaa = Any Amino Acid
<221> NAME/KEY: VARIANT
<222> LOCATION: (1)...(34)
<223> OTHER INFORMATION: Xaa = Any Amino Acid

<400> SEQUENCE: 33

Gly Ser Arg Arg Ala Ser Val Gly Ser Xaa Xaa Xaa Xaa Xaa Xaa Xaa
1               5                  10                  15

Xaa Xaa Xaa Xaa Xaa Xaa Xaa Xaa Xaa Gly Ser Pro Gly Ile His
            20                  25                  30

Arg Asp

<210> SEQ ID NO 34
<211> LENGTH: 4
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (3)...(3)
<223> OTHER INFORMATION: Xaa = Any Amino Acid
<221> NAME/KEY: VARIANT
<222> LOCATION: (1)...(4)
<223> OTHER INFORMATION: Xaa = Any Amino Acid
<221> NAME/KEY: VARIANT
<222> LOCATION: (1)...(4)
<223> OTHER INFORMATION: Xaa = Any Amino Acid

<400> SEQUENCE: 34

Arg Arg Xaa Ser
1

<210> SEQ ID NO 35
<211> LENGTH: 4
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (3)...(3)
<223> OTHER INFORMATION: Xaa = Ala or Gly
<221> NAME/KEY: VARIANT
<222> LOCATION: (1)...(4)
<223> OTHER INFORMATION: Xaa = Any Amino Acid
<221> NAME/KEY: VARIANT
<222> LOCATION: (1)...(4)
<223> OTHER INFORMATION: Xaa = Any Amino Acid

<400> SEQUENCE: 35

Arg Arg Xaa Ser
1

<210> SEQ ID NO 36
<211> LENGTH: 5

```
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (4)...(4)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid

<400> SEQUENCE: 36

Ser Arg Arg Xaa Ser
 1               5

<210> SEQ ID NO 37
<211> LENGTH: 5
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (3)...(3)
<223> OTHER INFORMATION: Xaa = Any Amino Acid
<221> NAME/KEY: VARIANT
<222> LOCATION: (5)...(5)
<223> OTHER INFORMATION: Xaa=Gly or Ala
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid

<400> SEQUENCE: 37

Arg Arg Xaa Ser Xaa
 1               5

<210> SEQ ID NO 38
<211> LENGTH: 6
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (5)...(5)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid

<400> SEQUENCE: 38

Gly Ser Arg Arg Xaa Ser
 1               5

<210> SEQ ID NO 39
<211> LENGTH: 5
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (3)...(3)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid
<221> NAME/KEY: VARIANT
```

-continued

```
<222> LOCATION: (1)...(5)
<223> OTHER INFORMATION: Xaa = Any Amino Acid

<400> SEQUENCE: 39

Arg Arg Xaa Ser Val
 1               5

<210> SEQ ID NO 40
<211> LENGTH: 6
<212> TYPE: PRT
<213> ORGANISM: Artificial Sequence
<220> FEATURE:
<223> OTHER INFORMATION: synthetic or recombinant peptide motif
<221> NAME/KEY: VARIANT
<222> LOCATION: (3)...(3)
<223> OTHER INFORMATION: Xaa = Any Amino Acid
<221> NAME/KEY: VARIANT
<222> LOCATION: (6)...(6)
<223> OTHER INFORMATION: Xaa=Gly or Ala
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid

<400> SEQUENCE: 40

Arg Arg Xaa Ser Val Xaa
 1               5
```

US 8,435,490 B2

SMALL PEPTIDES SPECIFICALLY BIND TO COLORECTAL CANCERS

GOVERNMENT FUNDING

This invention was made using funds from the U.S. government, particular grants from the National Cancer Institute. The U.S. government retains certain rights in the invention as provided in CA077057-09A2 and CA095323-14.

TECHNICAL FIELD OF THE INVENTION

This invention is related to the area of cancer management. In particular, it relates to diagnostic and therapeutic approaches to cancer management.

BACKGROUND OF THE INVENTION

Recent landmark discoveries have convincingly documented the extensive genetic heterogeneity among human cancers, particularly colorectal tumors, by establishing the existence of a small number of frequently mutated gene "mountains" and a much higher number of gene "hills" mutated at much lower frequencies [1,2]. This high degree of diversity among human colorectal cancers suggests that individualized treatment strategies hold great promise in successful clinical intervention. Several anticancer immunotherapies are currently in use, including Herceptin, Rituxin, and Avastin, a monoclonal antibody directed against VEGF (vascular endothelial growth factor) that is approved for colorectal cancer treatment [3-9].

Radioimmunotherapy (RIT) is an emerging technology with thus far only two FDA-approved protocols, both directed against non-Hodgkin's lymphoma (NHL). Each protocol utilizes a monoclonal antibody directed against the CD20 B-cell marker and can deliver $^{90}$Y (Zevalin) or $^{131}$I (Bexxar), each of which generates electrons (beta particles) that damage DNA, resulting in cell death [10,11]. Currently, no RIT has yet been approved for the treatment of colorectal cancer [12].

There is a continuing need in the art to develop new ways to detect, image, locate, and ablate cancers.

SUMMARY OF THE INVENTION

According to one aspect of the invention a method is provided for delivering a radioactive isotope to a colon adenocarcinoma cell. A radioactive isotope-labeled peptide is administered to a colon adenocarcinoma cell. The peptide is a substrate for protein kinase A (PKA) and comprises the motif R-X-S/T or R-R/K-X-S/T. The peptide binds to the cell and the radioactive isotope is internalized and transferred to cellular proteins.

Another aspect of the invention is a peptide which has at least 90% homology to a sequence selected from the group consisting of SEQ ID NO: 1-28. The peptide is able to bind to the surface of a colon adenocarcinoma cell at least 50-fold more than to a normal colon cell.

According to another aspect of the invention a method is provided for screening a protein kinase A (PKA) substrate peptide for its ability to deliver radioactive isotope to a colon adenocarcinoma cell. A radioactive isotope-labeled peptide is contacted with the colon adenocarcinoma cell of a patient. Either binding of the peptide to the colon adenocarcinoma cell or transfer of the radioactive isotope from the peptide to proteins of the adenocarcinoma cell of the patient are measured, or both.

The present invention thus opens up new avenues for management of cancer, in which small peptide molecules, which can be readily synthesized or made in recombinant cells, are able to replace antibodies as targeting agents.

These and other embodiments which will be apparent to those of skill in the art upon reading the specification provide the art with

BRIEF DESCRIPTION OF THE DRAWINGS

(FIG. 3A) Nine $^{32}$P-labeled different decapeptides, varying from one another by only one to three amino acids, were incubated with Caco-2 cells for two hours, the cells washed three times, and counts remaining bound to the cells are shown as a percentage of the total amount of counts for each decapeptide used. Amino acid substitutions for each variant (relative to MA1) are underlined and bolded. (FIG. 3B) The variants, MA1, MA4, and MA5 were incubated with Caco-2 cells for intervals varying from five minutes to two hours, washed, the adherent cells dissolved in gel loading buffer and an aliquot run on a 10%-20% gradient polyacrylamide-SDS gel. The three lanes marked "24h" (lanes 5, 10, and 15) were incubated with the respective labeled decapeptides (MA1, MA4, MA5) for two hours, washed, and the cells incubated with complete medium for 24 hours. The cells were treated as described for the other lanes of this figure.

FIGS. 4A-4D. The majority of the $^{32}$P-labeled decapeptide MA5-bound molecules are released from Caco-2 cells. (FIG. 4. A) The 32P-labeled decapeptide MA5 was incubated for two hours with five different cell lines, the cells were washed, and complete medium was added. Following a 24 hour incubation, the number of counts per minute released into the medium (R) as well as the number of counts remaining bound to the cells (B) were determined. Each bar shows the mean and one standard deviation of triplicates wells. (FIG. 4. B) Time course for the release and retention of the $^{32}$P-labeled decapeptide MA5. MA5 was incubated for two hours with Caco-2 cells, the cells washed, and the cpm released (dashed line) as well as remaining bound (solid line) to the cells determined for time intervals post-washing. Each point shows the mean plus/minus one standard deviation of triplicate determinations. (FIG. 4. C) Radioactive well contents described as bound (solid line) in FIG. 4B were run on a 16.5% polyacrylamide-SDS gel and exposed to film. Immediately after washing (i.e., at 0 hours), the majority of the counts were visualized as $^{32}$P-peptide. Over the next 48 hours, the peptide counts greatly diminished, with the majority of bound radioactivity incorporated into cellular proteins. (FIG. 4. D) Aliquots of medium containing the released (dotted line) $^{32}$P-peptide MA5 were assayed at time intervals after washing, as described in FIG. 4B. As time progressed, more of the $^{32}$P-peptide was released, reaching a plateau by 24 hours after washing.

DETAILED DESCRIPTION OF THE INVENTION

Figure 1:
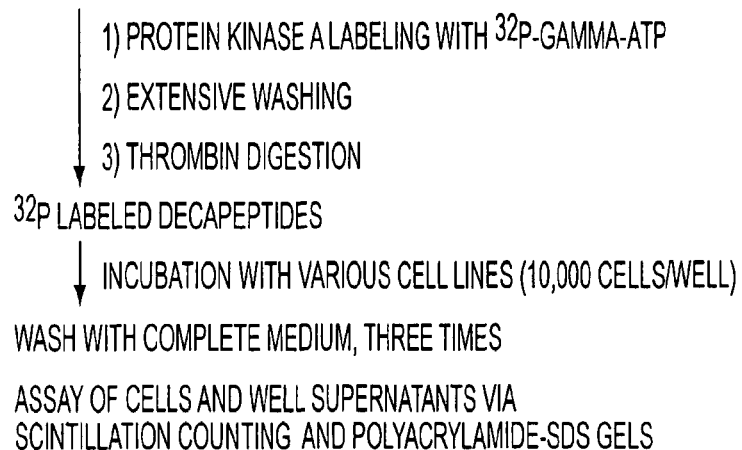
FIG. 1. Schematic diagram of experimental approach. A bacterial recombinant expression system produced various gluthathione-S-transferase decapeptide fusion proteins which were bound to glutathione and labeled with $^{32}$P utilizing protein kinase A (PKA). After washing, the labeled decapeptides were recovered after thrombin digestion and incubated at various times with several different cell lines.

The inventors have developed a general strategy for delivering therapeutic or diagnostic moieties to a cancer cell. A class of peptides have been found which specifically bind to colon adenocarcinoma cells and deliver a radioisotope to cellular proteins of the colon adenocarcinoma cells. Surprisingly, peptide substrates of protein kinase A (PKA) bind to colon adenocarcinoma cells preferentially relative to other cancer cells lines and relative to cell lines derived from normal tissues, including normal colon.

The peptides can be labeled with any desired radionuclide according to methods known in the art. Most conveniently, these can be labeled with isotopes of P, such as $^{32}$P or $^{33}$P using PKA. If a non-phosphorus radionuclide is desired, a synthetic chemistry scheme for attaching is used. Other isotopes which are used in radiomedicine include technetium-99m, rubidium-82, thallium-201 chloride, fluoro-deoxy glucose incorporating F-18, lutetium-177, Ytrrium-90, iodine-131, phosphorus-32, boron-10, actinium-225, bi-213. Any of these or other radionuclides can be attached to the peptides of the present invention. Different radionuclides will be selected depending on desired use as a therapeutic or diagnostic agent. Possible therapeutic radionuclides include those that decay to provide Auger electrons, beta-particles, or alpha-particles. Different radionuclides will be selected depending on the type of imaging device that will be used. Possible imaging techniques which may be used include Pet, SPECT, MRI, CAT, etc. Those of skill in the art can readily determine the appropriate isotope to use.

The peptides of the present invention appear to be quite specific for colon adenocarcinoma, particularly relative to normal colon tissue. The relative difference in the amount and/or rate of binding between tumor and normal tissue will typically be reflected in safety and diminished side-effects. In addition, it will be reflected in the usefulness for imaging, with greater relative differences providing increased clarity and contrast. The peptides to be used for radiotherapy or radioimaging will bind at least 20-fold, at least 50-fold, at least 100-fold, at least 150-fold, or at least 200-fold more to cancer cells than to normal cells of the same cell tissue type.

Peptides of the invention are typically between 4 and 50 amino acid residues, or between 4 and 35 amino acid residues, or between 9 and 30 amino acid residues, or between 9 and 15 amino acid residues. These are significantly smaller than full antibodies and even of antibody fragments and derivatives, such as single chain antibodies. The smaller size provides increased penetration to tumors, which can be a distinct therapeutic benefit. In some situations, however, it may be desirable to link additional amino acid residues to the peptides, for example, to provide additional functionalities. For example, it may be desirable to attach a biological toxin to the peptide. Many biological toxins are known and any can be used if appropriate to provide a desired cell killing effect. Other non-amino acid moieties may also be added to the protein for desired benefits. For example, a fluorophore may be desired and can be used.

Peptides that will be administered to a patient for imaging or therapeutic purposes will be safe and suitable for administration. Such administration may typically by injection into the blood stream or into particular organs. Alternatively, the administration can be subcutaneously, intraperitoneally, intramuscularly, intradermally, sublingually, orally, etc. The preparations of peptides can be isolated and purified from other peptides. The preparations can be sterile and/or free of pyrogens. The peptides can be made by synthetic chemistry, semi-synthetic chemistry, recombinant organisms, or by isolation from natural sources and subsequent processing to yield the desired peptide products. Means for synthesizing peptides, for example in an automatic peptide synthesizer are well within the skill of the art. Recombinant techniques for generating peptides are also well known to the skilled artisan.

Any peptide can be used, including those that are shown in SEQ ID NO: 1-40. Preferably the peptide will share at least 90% identity with the sequence shown in SEQ ID NO: 1-40. The peptide may have additional portions, as well, as discussed above, for example to provide additional functionality.

Peptides can be packaged individually or in libraries to facilitate screening for a good match between a particular patient and a peptide. The peptides may be packaged with a radionuclide attached or the radionuclide may be provided separately. Kits for attaching a radionuclide may contain both one or more peptides and an enzyme, such as PKA for attaching a radionuclide the peptide.

Decapeptides that can be labeled with a high energy (1.7 Mev) beta emitter ($^{32}$P) and can bind avidly to several different adenocarcinoma cell lines, efficiently delivering this potential tumor-ablating material to the cells. The decapeptides, termed MA for Modified Adjuvant, are protein kinase A substrates. When labeled with a tumor-ablating material such as $^{32}$P, these peptides bind to and transfer the radioisotope to a cell line after one to two hours of incubation. Moreover, we have shown that transfer of isotope from these decapeptides is restricted to cell types derived from primary colon adenocarcinomas. For example, exposure of certain colon cancer cell lines (e.g., Caco-2) to the most avidly binding labeled peptide, MA5, for a two-hour period resulted in the transfer of a radioactive dose of over 29 counts per minute per cell after a two hour incubation, wash, and immediate determination of the retained radioactivity.

The incubation of $^{32}$P-labeled decapeptide with certain cell lines resulted in large amounts of peptide being retained after a two-hour incubation, but a substantial proportion of this bound peptide was released after an overnight incubation. For example, after incubation of the labeled variant MA5 with Caco2 cells for two hours, three wash steps, and overnight incubation in medium, 88% of the originally retained $^{32}$P isotope was released. However, the 12% that was retained by cells still represented 5.8 cpm per cell, extrapolating to over 8,300 counts per cell per day. In addition, radioactivity that was still retained by cells after overnight medium incubation was permanently incorporated into a variety of cellular proteins, as demonstrated by polyacrylamide gel electrophoresis of post-exposure cellular lysates Among 16 cell lines assayed for their ability to bind the decapeptides, five demonstrated very high retention of isotope after two-hour incubation. Although all five of these lines released from 63% to 88% of this radioactivity after an overnight incubation, the amount of isotope that was retained overnight was still substantial. All five of these cell lines were derived from colorectal adenocarcinomas. The eleven cell lines that did not bind the radioactively labeled decapeptide MA5 were derived from a variety of tissue origins. These included squamous cell carcinomas of the cervix, lung, breast, and a fibrosarcoma, as well as normal kidney, colon, and esophageal tissues.

The majority of approved immunotherapeutic regimens for cancer involve an antibody directed against a specific cellular molecule [27]. These agents can function by binding to the cell surface and may utilize ADCC, complement activation, or cellular apoptosis. The antibodies may also be coupled to a tumor-ablating agent, such as toxins or radioisotopes [14]-[18]. The addition of isotope to peptides, and their use for both diagnostic and therapeutic purposes, is an active area of biomedical research [19]-[22]. Our work utilizes protein kinase A (PKA) substrates labeled with $^{32}$P isotope. A high-energy beta-emitting radioisotope results in an electron path length range of up to 5 mm, permitting substantial penetration of solid tumors. Due to a predicted "bystander" effect, one beta particle will penetrate hundreds or thousands of cells within the tumor, even those not directly binding the decapeptide. Moreover, since the molecular weights of these minuscule decapeptides proteins are far lower than the exclusionary molecular weight limit of the filtering kidneys, these peptides should be rapidly eliminated in the urine, leading to reduced systemic toxicity. Thus, it should be feasible for both a radioactive dose and unbound radioactivity to be eliminated easily and in a relatively short period of time. We anticipate that additional known enzyme substrates can be identified as potential vehicles for the specific delivery of anti-tumor agents to cancer cells and that potential cancer therapeutic regimens employing this peptide or other similar substances might be a general strategy for peptide binding therapy.

Nineteen different small peptides up to 34 amino acids in length have been recombinantly produced, each containing an insert up to 17 residues long, which can be labeled at a conserved nine amino acid substrate using $^{32}$P and protein kinase A (PKA). These $^{32}$P-labeled peptides bind with unique affinities to cell lines established from different colon adenocarcinomas and permanently transfer radioisotope to cellular proteins after two hours of incubation. The most efficiently binding peptide results in the permanent uptake of $^{32}$P by colon cancer cells over 150 times higher than by cell lines derived from other cancers or normal tissues. In addition, one $^{32}$P-labeled peptide bound to all cell lines tested, but $^{32}$P was processed and permanently incorporated only by cell lines derived from colon adenocarcinomas, implying that only this type of cancer cell possesses the machinery necessary for this processing step. The nineteen different peptides shown in FIG. 6 were selected from an initial screening panel containing only 25 peptides. This surprisingly high rate of obtaining successful peptides enhances the likelihood that this strategy for individualized therapy development will be feasible. Finally, a competitive binding assay using cold and $^{32}$P-labeled synthetic MA11 peptide demonstrated that non-phosphorylated peptide competes very efficiently for binding to Caco2 cells.

Most currently approved cancer immunotherapeutic regimens use an antibody directed against a known cellular molecule; the antibody may optionally be coupled to a tumor-ablating agent, such as a radioisotope or a toxin [14-18]. Only two radioimmunotherapeutic (RIT) treatments are presently FDA-approved; both are directed against non-Hodgkin's lymphoma utilizing $^{131}$I (Bexxar) or $^{90}$Y (Zevalin) via the cell-killing activity of emitted electrons. $^{32}$P radioisotope is a pure beta emitter, and as shown in Table 1, it has many properties that compare favorably to $^{131}$I and $^{90}$Y, in addition to being readily available and relatively inexpensive. One advantage of using beta particles to kill tumor cells is that their path range of up to 5 mm results in a large number of cells being penetrated by each electron, leading to a cumulative "bystander effect" due to crossfire from neighboring labeled cells.

TABLE 1

Comparison of Properties of Radioactive Beta Emitting Radioisotopes.

| Radioisotope | Emits | Maximum Beta Energy (MeV) | Range | Half-life (days) |
|---|---|---|---|---|
| $^{131}$Iodine | Beta | 0.6 | 1.6 mm. (avg.) | 8 |
| $^{90}$Yttrium | Beta | 2.3 | 5 mm. (avg.) | 2.7 |
| $^{32}$P | Beta | 1.7 | up to 5 mm. | 14.3 |

Bexxar ($^{131}$I-anti-CD20) and Zevalin ($^{90}$Y-anti-CD20) are FDA-approved for the treatment of non-Hodgkin's lymphoma.

A very active area of biomedical research focuses on the coupling of radioisotope to peptides, as well as its use in diagnostic and therapeutic applications [19-22]. Our proposed application of $^{32}$P-labeled small peptides in peptide binding therapy suggests a number of advantages over traditional RIT based on monoclonal antibodies. For example, smaller therapeutic molecules are expected to provide better tumor penetration, and the average small peptide molecular weight of less than 4,000 Da is less than 3% of the size of an antibody molecule [23]. Radioactive halogens such as $^{131}$I can be processed and released prematurely by cells, while the $^{32}$P delivered by these small peptides is permanently incorporated into cancer cell proteins [24]. A small peptide is less likely to incite the type of host anti-protein response that can develop when using the much larger antibodies, and the absence of an Fc immunoglobulin fragment should result in less nonspecific binding by the liver. The radioisotope $^{32}$P has a long history of clinical use dating to the early 1930's, while today it is still used to treat polycythemia and essential thrombocythemia [25]. There is a clear need for the development of effective new treatments for colorectal cancer [26]. Our work suggests that an extremely large library of different small peptides, each with unique binding and $^{32}$P transfer abilities, can be readily produced either chemically or biologically, thus increasing the feasibility of developing individualized treatment regimens for different patients. Cancer has been shown to be a highly heterogeneous disease, thus the development of these unique peptide binding therapies could greatly facilitate individualized patient treatments.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Production of the recombinant $^{32}$P-labeled peptides. As described in FIG. 5, PCR generated products consisting of 17 random codons flanked by BamHI sites were cloned into the BamHI site of pGEX-2TK (GE Healthcare). After transformation into DH5α bacteria, isolated clones were grown overnight in LB-amp broth, diluted 1/10 in same, grown for two hours, IPTG added to 1 mM, and grown at 37° C. for five hours. Ten ml of culture were centrifuged and resuspended in 1 ml of 1×TBS containing 100 μg/ml lysozyme. After two freeze-thaw cycles, the lysate was centrifuged and mixed with 100 μl Sepharose-Glutathione for one hour, washed three times with 1×TBS, and the bound recombinant fusion proteins labeled using $^{32}$P-γ-ATP and protein kinase A (PKA) according to the manufacturer's instructions (Sigma, St. Louis, Mo.). The pellet was washed three times with 1×PBS and the labeled peptide was cleaved and released into the supernatant using thrombin (GE Healthcare). For each recombinant peptide produced and assayed, the DNA sequence of the insert in the expression plasmid was determined.

Production of the $^{32}$P-labeled decapeptides. Different DNA oligomers were cloned into pGEX-4T-1 (GE Healthcare) which yield various decapeptides after thrombin cleavage designated MA1 through MA9 (Modified Adjuvant). The protein sequences are: MA1, GSRRASVGSA (SEQ ID NO: 1); MA2, GSRGASVGGA (SEQ ID NO: 2); MA3, GSR-RGSVGSA (SEQ ID NO: 3); MA4, GSRRGSVASA (SEQ ID NO: 4); MA5, GSRRASVASA (SEQ ID NO: 5); MA6, GSRRASVGSG (SEQ ID NO: 6); MA7, GSRGGSVGSA (SEQ ID NO: 7); MA8, GSRGGSVASA (SEQ ID NO: 8); MA9, GSRGGSVGSG (SEQ ID NO: 9). DH5-α bacteria containing these clones were grown overnight in LB (containing 100 μg/ml ampicillin), diluted 1/10 in LB-Amp and grown at 37° C. for two hours. IPTG was added to 1 mM and the culture grown at 37° C. for five hours. Ten ml of each culture were centrifuged and the cell pellet resuspended in 1×TBS containing 100 μg/ml lysozyme. After two cycles of freeze-thaw, the lysate was centrifuged and the supernatant was mixed with 100 μl of Sepharose-Glutathione for two hours at RT. Each pellet was washed three times with 1×TBS, and the bound recombinant fusion proteins were labeled with $^{32}$P using protein kinase A (PKA) and $^{32}$P-γ-ATP according to the manufacturer's instructions (Sigma, St. Louis, Mo.). The pellet was washed four times with 1×PBS and the labeled decapeptide was cleaved and released into the supernatant with thrombin (GE Healthcare).

Assay of the binding of $^{32}$P-labeled decapeptides to cell lines: Cell lines were grown in complete medium containing 10% bovine fetal serum (heat inactivated). In each well of a 96-well plate, 10,000 cells from various cell lines were grown overnight in complete medium. Ten μl of the labeled-peptide in 1×PBS and 90 μl of complete medium were added to each well and incubated at 37° C. at various times of up to two hours. The peptide-medium was removed and one μl added to 100 μl gel loading buffer and counted by scintillation counting for the probe control or run on a polyacrylamide-SDS gel (Biorad). The adherent cells were briefly and gently washed with complete medium three times and some wells were assayed immediately by adding 100 μl of gel loading buffer to each well and run on a gel or counted in a scintillation counter. Other wells had 100 μl complete medium added and incubated for a further time period. Samples were either counted in a liquid scintillation counter or run on polyacrylamide-SDS gels, exposed to x-ray film, and the film developed.

Assay of the binding of $^{32}$P-labeled peptides to cell lines. Cell lines were grown in complete medium containing 10% heat inactivated bovine fetal serum. In each well of a 96-well plate, 10,000 cells from various cell lines were grown overnight. Ten μl of the $^{32}$P-labeled peptide in 1×PBS and 90 μl complete medium were added to each well and incubated at 37° C. for two hours. The peptide-medium was removed and one μl added to 100 μl gel loading buffer for scintillation counting for the probe quantitation or run on a 10%-20% polyacrylamide-SDS gel (Biorad). The adherent cells were briefly and gently washed with complete medium three times and some wells were assayed immediately by adding 100 μl of gel loading buffer to each well and run on a gel or counted in a scintillation counter. Other identically treated wells had 200 μl complete medium added and incubated at 37° C. for an additional 24 hours. The medium was removed and 100 μl gel loading buffer added and the samples run on a gel or counted as described above.

Production of synthetic $^{32}$P-labeled peptide. The 12 amino acid peptide MA11 was chemically synthesized and 0.2 µg was labeled as described above using 300 µCi of $^{32}$P-γ-ATP and 30 units of protein kinase A (PKA). After a five hour labeling reaction, the mixture was microfuged though a Microcon-10 unit to remove the enzyme from subsequent binding assays. For the competitive binding assay, 0.005 µg of $^{32}$P-labeled peptide MA11 was added to a well containing 10,000 Caco2 cells and a designated quantity of cold, non-phosphorylated MA11. After incubation for one hour, the adherent cells were gently washed and the well contents counted.

EXAMPLE 2

Making Peptides

We have identified nine decapeptides, differing from one another by only a few amino acids, that when labeled with $^{32}$P can bind to a number of colorectal carcinoma cell lines. All decapeptides contain a protein kinase A (PKA) substrate sequence and are designated as MAs (Modified Adjuvant). FIG. 1 is a schematic representation of the production of the $^{32}$P-labeled peptides and the experimental design of assays to measure binding of peptides to cell lines.

Figure 5:
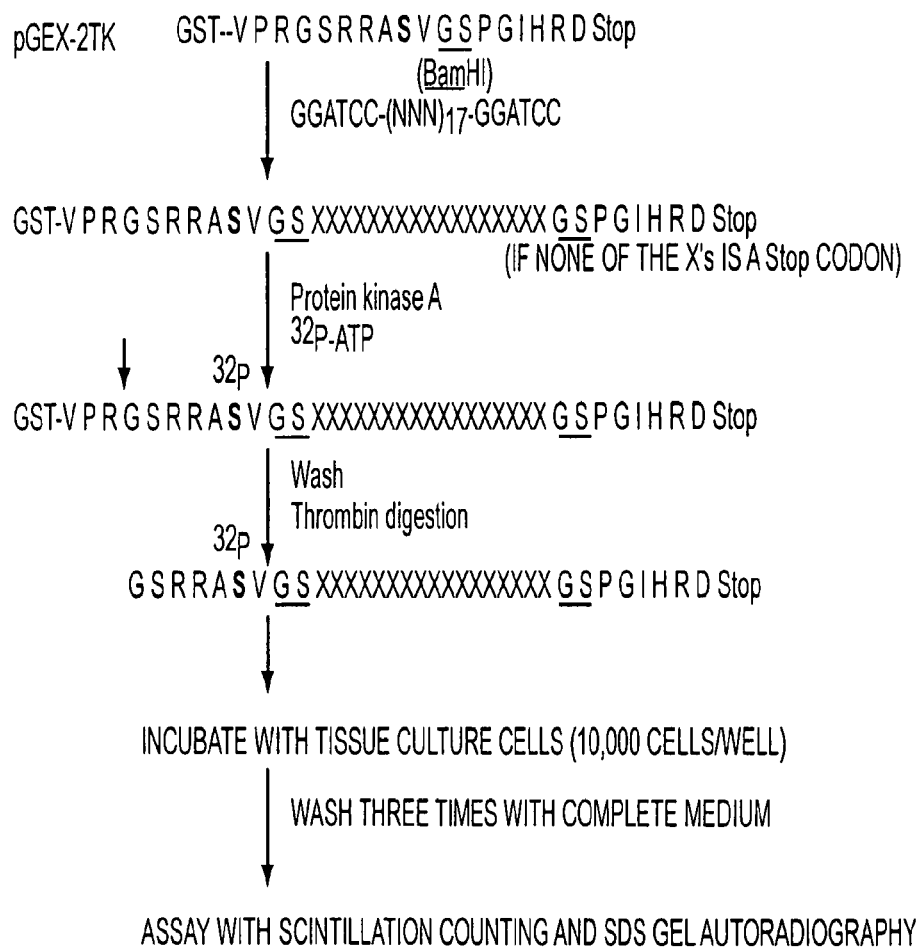
FIG. 5. Schematic diagram of experimental approach. A PCR product containing 17 random codons was inserted into the BamHI site of pGEX-2TK producing various glutathione-S-transferase fusion proteins which were bound to glutathione-sepharose, and labeled with $^{32}$P using protein kinase A (PKA). After washing and thrombin digestion, the labeled peptides were incubated with several different cell lines and assayed.

Production of $^{32}$P-labeled peptides and binding to colon adenocarcinoma cells. We produced and identified an additional series of peptides, up to 34 amino acids in length, whose amino acid sequences dramatically alter their ability to bind to and permanently facilitate $^{32}$P incorporation into cells. FIG. 5 is a schematic representation of the experimental design, illustrating the cloning of a DNA fragment containing 17 randomly generated codons into the BamHI restriction enzyme site of pGEX-2TK. After bacterial transformation, individual clones were selected and expanded to produce a diverse set of $^{32}$P-labeled peptides. If no stop codons were present in the random DNA sequence, then a 34-residue peptide was generated, flanked at its amino end by the 9-residue protein kinase A (PKA) labeling motif and at its carboxy terminus by an 8-residue sequence. As expected, in several clones, a stop codon was inserted, resulting in truncated peptides; however, all of these truncated peptides contained the protein kinase A (PKA) substrate moiety. These diverse peptides were incubated with several different cell lines for two hours, adherent cells were washed three times, and radioactivity remaining bound to cells was assayed either immediately, or following overnight incubation in complete medium.

EXAMPLE 3

Cell Binding and Isotope Transfer to Proteins

Figure 2:
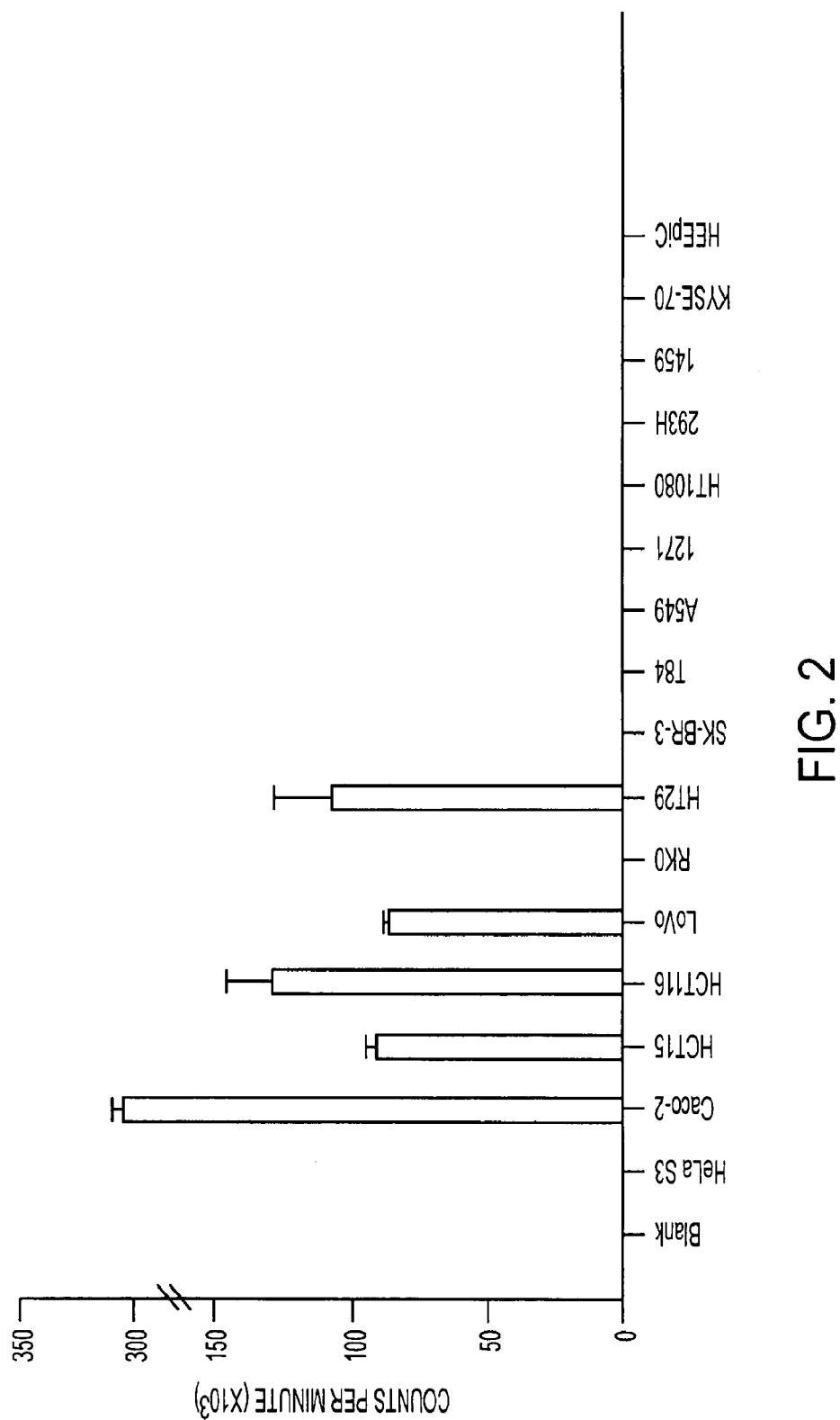
FIG. 2. Levels of binding of decapeptide MA5 to eighteen different cell lines. The $^{32}$P labeled decapeptide MA5 was incubated for two hours with 10,000 cells, washed three times, and the radioactive counts of the cells determined by scintillation counting. Seven cell lines demonstrated avid binding of MA5 and are shown as bar graphs of the mean and one standard deviation in triplicate wells. The remaining eleven cell lines, along with one blank well averaged only 365 cpm. These values are so small as to not be visible at the scale used in this figure. Further information on the individual cell lines is provided in the Supplemental Information.

FIG. 2 displays the number of $^{32}$P counts per minute (cpm) remaining bound to sixteen different cell lines and blank wells after a two hour incubation with MA5, the most efficient binding decapeptide (see below). The Caco-2 colon adenocarcinoma cell line retained the greatest number of radioactive counts after a two-hour incubation and subsequent washes with complete medium, the average value of triplicate wells equaling 298,639 cpm per 10,000 cells. HCT116 colon adenocarcinoma cells retained an average value of 131,998 cpm per 10,000 cells. Blank wells and nonbinding cell lines had mean values of less than 550 cpm; bars representing these values are not visible at the scale used in FIG. 2. For example, HeLa S3 cervical cancer cells only retained an average of 534 cpm per 10,000, HT1080 fibrosarcoma cells retained 367 cpm, and the human embryonic kidney cell line 293H retained 429 cpm per 10,000 cells.

Five of the sixteen cell lines demonstrated very strong retention of radioactivity when incubated with MA5 (Modified Adjuvant radioactive peptide) with all five of these being colon adenocarcinoma cell lines (Caco-2, HCT15, HCT116, LoVo, HT29). In contrast, the eleven nonbinding cell lines were mostly squamous cell lines derived from carcinomas of the cervix (HeLa S3), colon (RKO), lung (1271, A549), esophagus (KYSE-70), a fibrosacroma (HT1080), or cells cultured from normal kidney (293H), colon (1459), or esophagus (HEEpiC). Nonbinding cell lines included T84, derived from a colon adenocarcinoma metastatic to lung, and SK-BR-3, isolated from a breast adenocarcinoma. The ratio of cpm retained by Caco-2 (298,639) to the average of the eleven nonbinding cell lines (365) was 818:1. Caco-2 cells retained approximately 18% of the total radioactive counts present in the incubation well after two-hour incubation.

Nine MA variants were assayed for adherence to Caco-2 cells after two hours' incubation. The relative binding level and amino acid composition of each MA variant is displayed in FIG. 3A. Alteration of only one to three amino acids within the peptide resulted in retention differences as large as 70-fold, e.g., in variant MA2 vs. variant MA5.

Figures 3A, 3B:
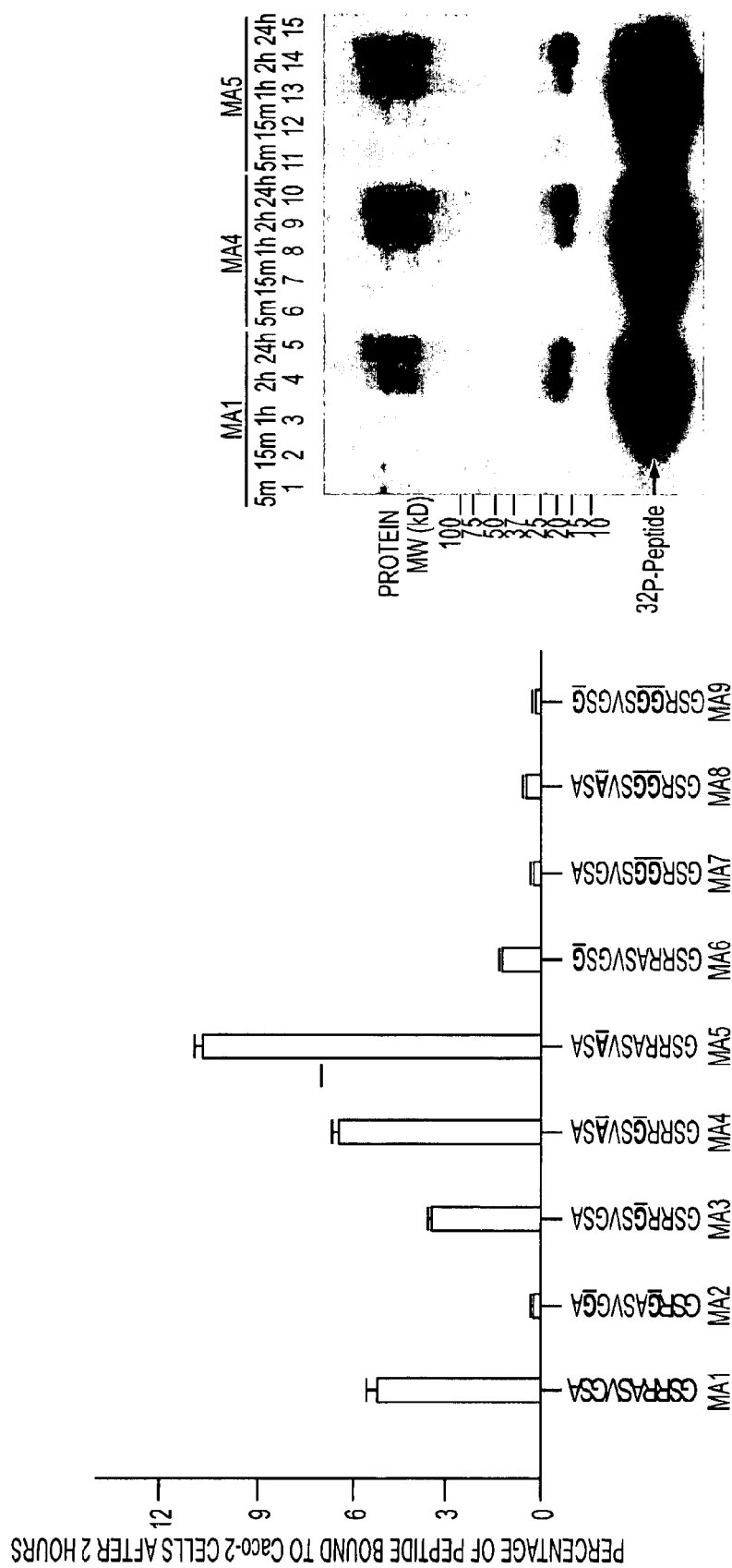
FIGS. 3A-3B. Relative levels of binding of nine 32P-labeled decapeptide variants.

To investigate how quickly $^{32}$P isotope could be transferred from the peptide variants and incorporated into cellular proteins, the three most avidly binding MAs (see FIG. 3A) were added to replicate wells containing Caco-2 cells, then washed away at varying time intervals and the cells and supernatant assayed. As shown in FIG. 3B, substantial percentages of these $^{32}$P-labeled variant decapeptides bound to cells within only a few minutes, with large amounts of radiolabeled cellular proteins appearing at two hours after exposing cells to the labeled peptides. Notably, a parallel experiment in which conditions described in FIG. 3 were duplicated, but washed cells were incubated overnight in complete medium (data not shown), still revealed similar levels of $^{32}$P-decapeptide release and retention for all nine MAs, as described for MA5 in FIG. 2.

The peptide binding, washing and assay experiment described for FIG. 2 was then repeated in the seven most avidly binding cell lines using MA5, except that after three washes of medium, 200 µl of complete medium was added to each well and the cells were incubated overnight at 37° C. FIG. 4A shows the cpm retained by cells or released into the medium after this overnight incubation. Approximately 88% of MA5 radioactive counts initially retained by the colon cancer cell lines was released into the medium, while approximately 12% of initially retained radioactive counts were retained by cells. Caco-2 cells retained the greatest number of counts, averaging 58,305 cpm in triplicate wells containing 10,000 cells each. This figure represents approximately 5.8 cpm, or 348 counts per hour, per cell (i.e., when extrapolated over a potential 2-week exposure period, equivalent to over 87,000 counts per cell).

FIG. 4B shows the time course of the release of MA5 from the Caco-2 adenocarcinoma cell line over a 48-hour time period. The majority of the total counts released over the 48 hour time period are released by nine hours of incubation. FIGS. 4C and 4D consist of two autoradiograms showing the locations of the radioactive molecules described in FIG. 4B on polyacrylamide-SDS gels. The sizes of the cellular radioactive proteins in the cells are shown in FIG. 4C; $^{32}$P-labeled MA5 released into the medium is shown in FIG. 4D. There is apparent agreement on the distribution and overall radioactivity levels in comparing FIG. 4B and FIGS. 4C and 4D. As soon as two hours after the introduction of the radioactive peptide, a substantial portion of the isotope appears to have been transferred to higher molecular weight proteins.

Figure 6:
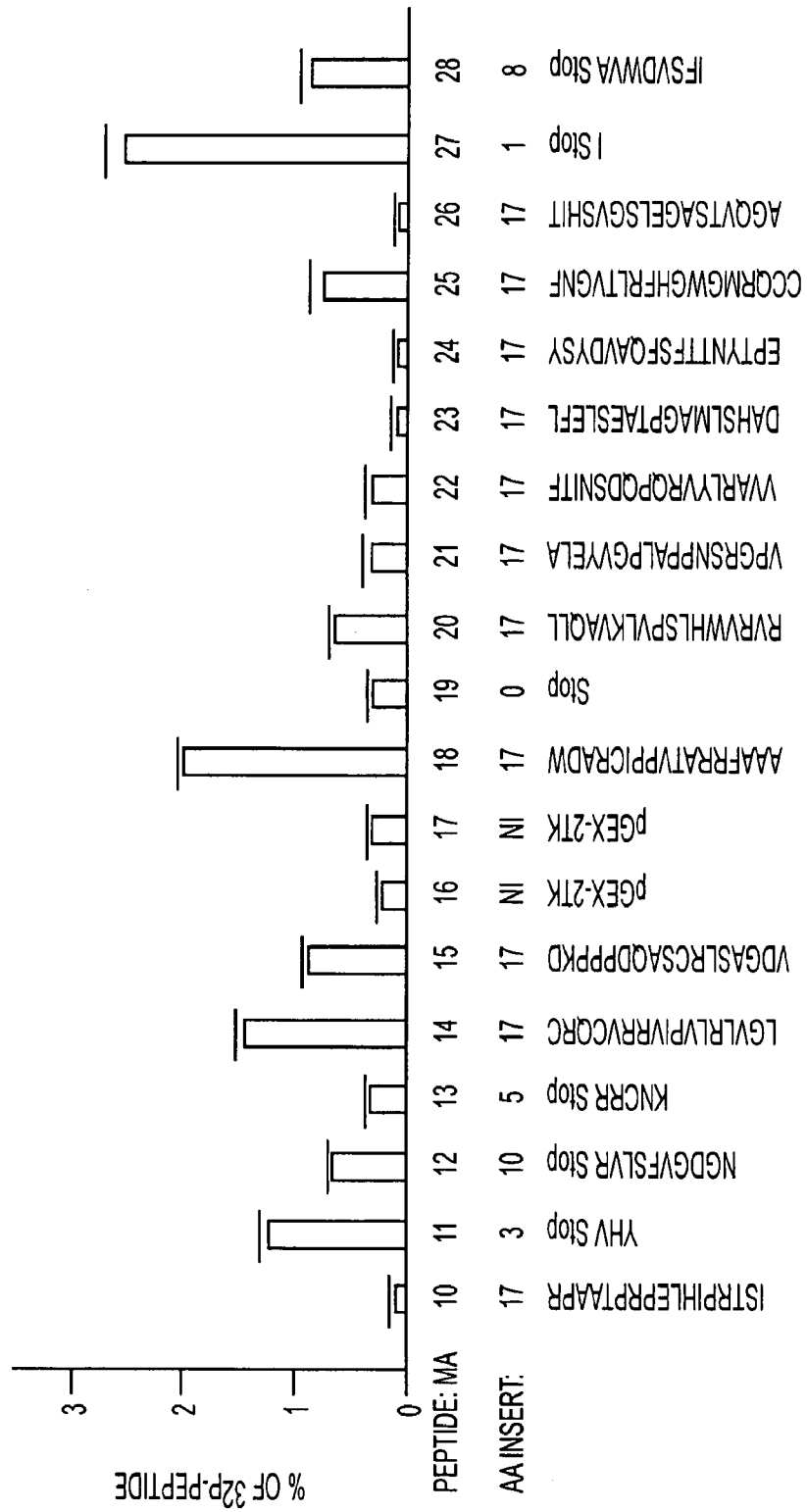
FIG. 6. Levels of binding of various $^{32}$P-labeled peptides to Caco2 cells. Different $^{32}$P-labeled peptides were incubated for two hours with 10,000 Caco2 cells, washed three times, and incubated in complete medium for 24 hours. The amount of $^{32}$P radioisotope that remained permanently incorporated into cellular proteins is shown as a percentage of uptake of the amount of peptide added to each cell culture well (mean plus one standard deviation). The number of amino acids present in each insert is shown and ranged from 0 to 17 amino acids. The amino acid sequence (SEQ ID NO: 10-28) of each insert is shown beneath the level of $^{32}$P incorporation attributed to each insert.

FIG. 6 shows the dramatic variation in levels of permanent $^{32}$P incorporation into the colon adenocarcinoma line Caco2 after washing and overnight medium incubation. As shown above, cells successfully binding decapeptides after two hours of incubation released up to 88% of their initially bound $^{32}$P into media after overnight incubation, but still permanently incorporated high levels of radioisotope into their proteins. The nineteen different peptides in FIG. 6 are designated MA (Modified Adjuvant) 10 through 28. Eleven of these 19 contain complete 17-residue inserts, with MA18 permanently transferring $^{32}$P to Caco2 cells over 37 times more efficiently than MA26. The most efficient permanent radioisotope incorporation into Caco2 cells occurred after incubation with MA27, which contains only one randomly inserted amino acid upstream of a stop codon. Peptides MA16 and MA17 were encoded by the original recombinant expression vector, leading to low levels of radioisotope incorporation.

EXAMPLE 4

Figure 7:
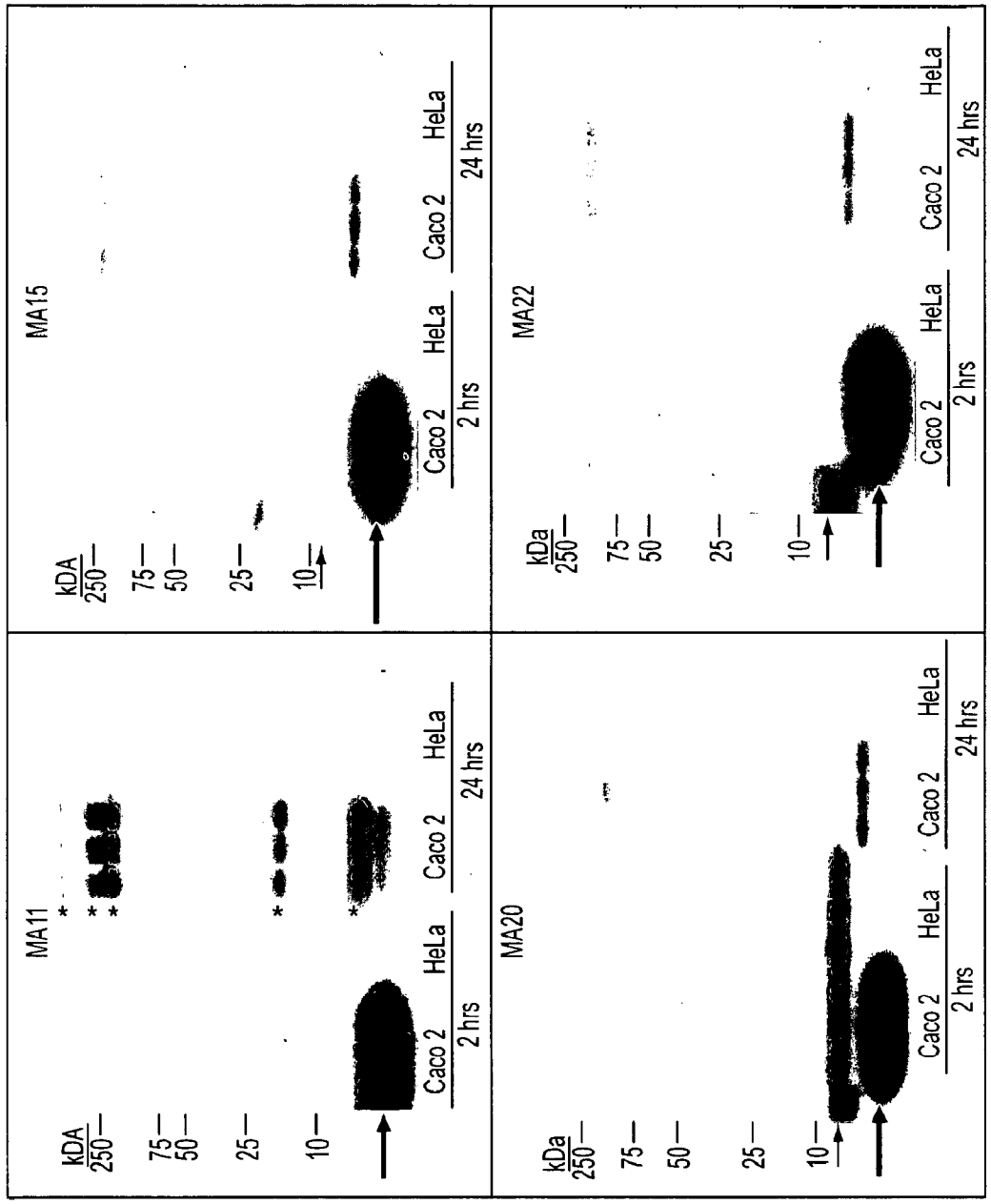
FIG. 7. SDS-polyacrylamide gels of $^{32}$P-peptide binding and radioisotope uptake by Caco2 cells. Four of the MA (Modified Adjuvant) $^{32}$P-peptides shown in FIG. 6 were incubated with triplicate wells of Caco2 or HeLa cells for two hours. After washing, 100 µl of gel loading buffer was added and the contents were run on SDS-polyacrylamide gels (designated as "2 hours"). Identical wells had complete medium added immediately after the washing step and were incubated for an additional 24 hours, and the well contents were then run on gels (designated as "24 hours"). Film was developed after an overnight exposure showing the apparent permanent incorporation of $^{32}$P into cellular proteins at 24 hours (marked by * in the MA11 panel). Peptide MA11 bound 215 times more avidly to Caco2 cells than to HeLa cells at two hours, and 150 times more avidly at 24 hours. Peptide MA20 bound well to both Caco2 and HeLa cells at two hours, but only Caco2 cells appeared to possess the cellular machinery needed to incorporate $^{32}$P into cellular proteins. The thin arrow shows the position of the $^{32}$P-labeled peptide, while the bold arrow shows the position of a relatively low molecular weight labeled intermediate that was not seen in the HeLa cells.

Visualization of $^{32}$P incorporation by gel autoradiography. Four peptides showing average levels of radioisotope incorporation were selected for further study; triplicate-well assays of these peptides are displayed in FIG. 7. Peptide MA11's insert contained three residues upstream of a stop codon, resulting in a peptide only 12 amino acids in length. Despite its relatively short length, this truncated peptide transferred $^{32}$P to Caco2 cells 215 times more efficiently than to the cervical tumor derived cell line HeLa at two hours. After washing and overnight incubation in medium, radioactivity retained by Caco2 cells was more than 150 times greater than that retained by HeLa cells. As shown in FIG. 7, most $^{32}$P bound to Caco2 cells was present in a low-molecular weight (LMW) component (bold arrow) at 2 hours, but at 24 hours most of this radioactivity had been incorporated into several different cellular proteins.

Similar results were observed for peptides MA15 and MA22, both of which contained 17-residue inserts for a total length of 34 amino acids, and both of which incorporated 23 times more $^{32}$P into Caco2 cells than into HeLa cells after overnight incubation (FIG. 7). Once again, both MA15 and MA22 showed an intensely radioactive LMW band (bold arrow) at 2 hours that had almost completely disappeared at 24 hours, with incorporation of the remaining $^{32}$P into cellular proteins. Originally, we assumed that this LMW band seen at 2 hours (bold arrow) represented intact bound $^{32}$P-labeled peptide. However, the 34 amino acid peptides MA15 and MA22 identified these intact 34-aa peptide precursors as distinct from the intense smaller MW band (bold arrows). Thus, we concluded that the smaller band was a rapidly processed small intermediate molecule, which diminished greatly over the ensuring 24 hours during which the $^{32}$P was being incorporated into the cellular proteins.

Peptide MA20 also contained a 17-residue insert. This peptide was especially noteworthy, since it was the only one tested that was able to bind to a cell line not derived from colon adenocarcinomas and provided key evidence suggesting a possible cellular processing mechanism. As shown in FIG. 7, MA20 bound at high levels to both Caco2 and to HeLa cells at two hours. However, the LMW band (bold arrow) seen with the other three peptides in FIG. 7 was only visible with Caco2 cells, but not with HeLa cells. After washing and overnight incubation, Caco2 cells appeared to have processed the LMW intermediate band (bold arrow) into cellular proteins, while HeLa cells apparently lacked the ability to complete this next step (i.e., no radioactive cellular proteins at these MWs were visualized, and all HeLa bound radioactivity was still at the same molecular weight as the originally bound $^{32}$P-labeled peptide (thin arrow)). The two bands (thin arrows, first lane of MA20 and MA22 gels) were the result of incubation of $^{32}$P-labeled peptide in medium containing serum for two hours at 37° C., and demonstrated apparent partial proteolysis of the peptide during that time.

EXAMPLE 5

Figure 8:
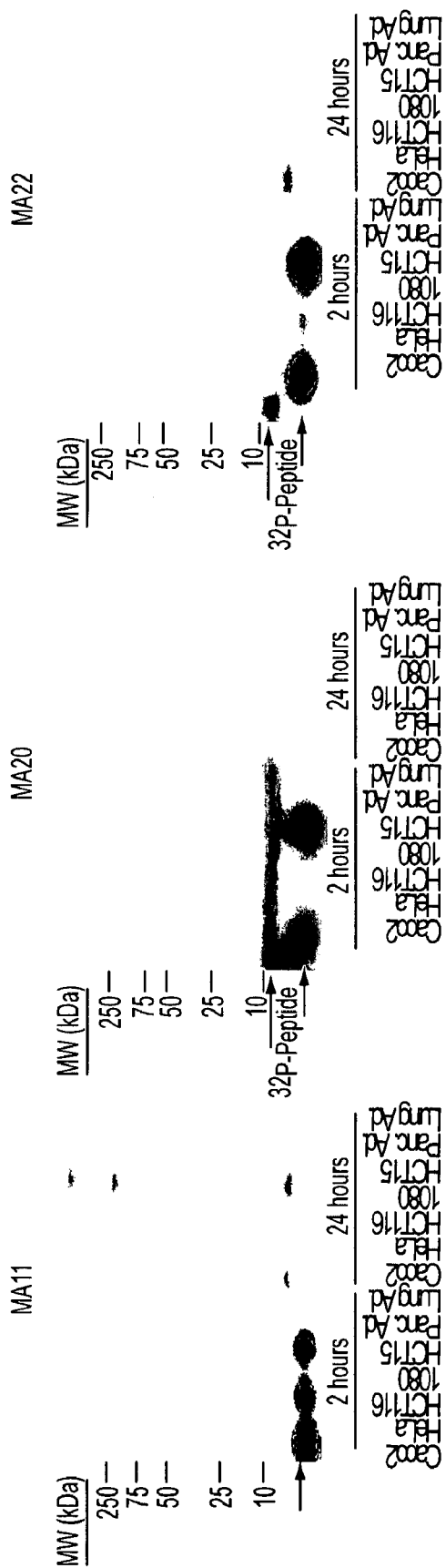
FIG. 8. Peptide MA20 binds to multiple cell lines, but $^{32}$P incorporation is only by colon adenocarcinoma derived lines. The $^{32}$P-labeled peptides MA11, MA20 and MA22 were incubated with seven different cell lines as described in FIG. 7. MA11 and MA22 bound to and had $^{32}$P radioisotope permanently incorporated by the three colon adenocarcinoma derived cell lines. MA20 significantly bound to all seven cell lines, including one derived from a pancreatic adenocarcinoma and one derived from a lung adenocarcinoma, but had significant levels of $^{32}$P permanently incorporated into cellular proteins only by the three colon adenocarcinomas. The thin arrow shows the position of the $^{32}$P-labeled peptide, while the bold arrow indicates the position of a relatively low molecular weight labeled intermediate that was only seen in colon adenocarcinoma cells.

Only colon adenocarcinoma cells process bound radioactivity into cellular proteins. FIG. 8 displays the results of incubating peptides MA11, MA20 and MA22 with seven different carcinoma cell lines at 2 hours and after overnight incubation. Peptides MA11 and MA22 exhibited strong binding and transfer of $^{32}$P only to the three colon adenocarcinoma lines (Caco2, HCT116, and HCT15) and not to cervical (HeLa), fibrosarcoma (1080), pancreatic or lung adenocarcinoma cells. MA20, in contrast, bound avidly to all seven cell lines, but its radioactivity was processed into the LMW band (bold arrow) and later into cellular proteins only by the three colon adenocarcinoma lines (Caco2, HCT116, and HCT15). HCT116 cells consistently bound, as well as processed into larger-MW bands, radioactivity from all three $^{32}$P-labeled peptides (MA11, MA20, and MA22) at a much lower rate than Caco2 and HCT15 cells, but incorporation into HCT116 cellular proteins was eventually visible on longer exposures (data not shown).

EXAMPLE 6

Figure 9:
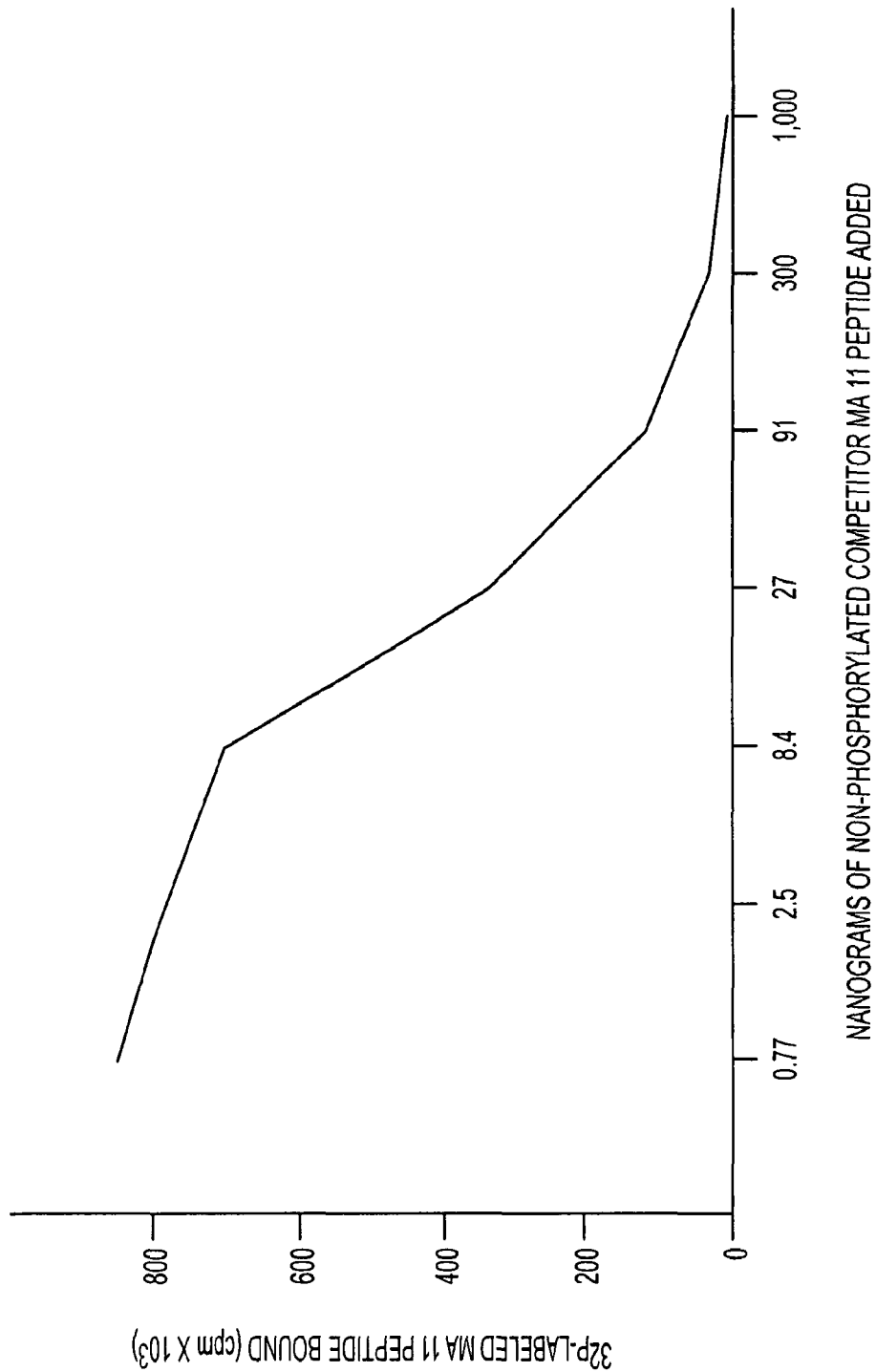
FIG. 9. Non-phosphorylated peptide effectively competes with $^{32}$P-labeled MA11 peptide in binding to Caco2 cells. Into each well containing Caco2 cells was added 0.005 µg $^{32}$P-labeled MA11 peptide and the indicated quantity of cold, non-phosphorylated MA11. After one hour of incubation, adherent cells were washed and the bound radioactive counts determined.

Non-phosphorylated peptide competes with $^{32}$P-labeled peptide for binding to Caco2 cells. The 12-aa peptide MA11 was chemically synthesized, labeled with $^{32}$P, and used in a competitive binding assay with Caco2 cells against varying amounts of cold, non-phosphorylated MA11 peptide. FIG. 9 illustrates that phosphorylation of this peptide was not required to successfully compete for binding to Caco2 cells, and that increasing amounts of cold competitor rapidly inhibited the amount of $^{32}$P-labeled peptide that bound to cells.

REFERENCES

The disclosure of each reference cited is expressly incorporated herein.
1. Sjoblom T, Jones S, Wood L D, Parsons D W, Lin J, et al. (2007) The consensus coding sequences of human breast and colorectal cancers. Science 314:268-274.
2. Wood L D, Parsons D W, Jones S, Lin J, Sjoblom T, et al. (2007) The genomic landscapes of human breast and colorectal cancers. Science 318:1108-1113.
3. Slamon D J, Leyland-Jones B, Shak S, Fuchs H, Paton V, et al. (2001) Use of chemotherapy plus a monoclonal antibody against HER2 for metastatic breast cancer that overexpresses HER2. N. Engl. J. Med. 344:783-792.
4. Romond E H, Perez E A, Bryant J, Suman V J, Geyer C E, et al. (2005) Trastuzumab plus adjuvant chemotherapy for operable HER2 positive breast cancer. N. Engl. J. Med. 353:1673-1684.
5. Tan-Chiu E, Yothers G, Romond E, Geyers C E, Ewer M, et al. (2005) Assessment of cardiac dysfunction in a randomized trial comparing doxorubicin and cyclophosphamide followed by paclitaxel, with or without trastuzumab as adjuvant therapy in node positive, human epidermal growth factor receptor 2-overexpressing breast cancer. J. Clin. Oncol. 23:7811-7819.

6. Davis T A, Grillo-Lopez A J, White C A, McLaughlin P, Czuczman M S, et al. (2000) Rituximab anti-CD20 monoclonal antibody therapy in non-Hodgkin's lymphoma: safety and efficacy of retreatment. *J. Clin. Oncol.* 18:3135-3143.
7. Rini B I, Rathmell W K (2007) biological aspects and binding strategies of vascular endothelial growth factor in renal cell carcinoma. *Clin. Cancer Res.* 13:741-746.
8. Van Cutsem E, Peeters M, Siena S, Humblet Y, Hendlisz A, et al. (2007) Open-label phase III trial of panitumumab plus best supportive care compared with best supportive care alone in patients with chemotherapy-refractory metastatic colorectal cancer. *J. Clin. Oncol.* 25:1658-1664.
9. Cilley J C, Barfi K, Benson A B, Mulcahy M F (2007) Bevacizumab in the treatment of colorectal cancer. *Expert. Opin. Biol. Ther.* 7:739-749.
10. Wiseman G A, White C A, Sparks R B, Erwin W D, Podoloff D A, et al. (2001) Biodistribution and dosimetry results from a phase III prospectively randomized controlled trial of Zevalin radioimmunotherapy for low-grade, follicular, or transformed B-cell non-Hodgkin's lymphoma. Crit. Rev. Oncol. Hematol. 39:181-194.
11. Vose, J M (2004) Bexxar: novel radioimmunotherapy for the treatment of low-grade and transformed low-grade non-Hodgkin's lymphoma. Oncologist 9:160-172.
12. Emir E E, Qureshi U, Dearling J L J, Boxer G M, Clatworthy I, et al. (2007) Predicting Response to radioimmunotherapy from the tumor microenvironment of colorectal cancers. Cancer Res. 67:11896-11905.
13. Abraham J M, Sato F, Cheng Y, Paun B, Kan T, et al. (2007) Novel decapeptides that bind avidly and deliver radioisotope to colon cancer cells. PLoS ONE 2:e964.
14. Kreitman R J (2006) Immunotoxins for targeted cancer therapy AAPS J. 8:532-551.
15. Kreitman R J, Pastan I (2006) Immunotoxins in the treatment of hematologic malignancies. Curr. Drug Targets 7:1301-1311.
16. Kreitman R J (2003) Recombinant toxins for the treatment of cancer. Curr. Opin. Mol. Ther. 5:44-51.
17. Boerman O C, Koppe M J, Postema E J, Corstens F H, Oyen W J (2007) Radionuclide therapy of cancer with radiolabeled antibodies. Anticancer Agents Med. Chem. 7:335-343.
18. Wu A M, Senter P D (2005) Arming antibodies: prospects and challenges for immunoconjugates. Nat. Biotech. 23:1137-1146.
19. Okarvi S M (2004) Peptide-based radiopharmaceuticals: Future tools for diagnostic imaging of cancers and other diseases. Med. Res. Rev. 24:357-397.
20. Aina O H, Sroka T C, Chen M L, Lam K S (2002) Therapeutic Cancer Targeting Peptides. Biopolymers 66:184-199.
21. Wangler C, Buchmann I, Eisenhut M, Haberkorn U, Mier W (2007) Radiolabeled peptides and proteins in cancer therapy. Protein Pept. Lett. 14:273-279.
22. Aina O H, Marik J, Liu, Lau D H, Lam K S (2005) Identification of novel targeting peptides for human ovarian cancer cells using "one bead one-compound" combinatorial libraries. Mol. Cancer. Ther. 4:806-813.
23. Reilly R M (2006) Radioimmunotherapy of solid tumors: The promise of pretargeting strategies using bispecific antibodies and radiolabeled haptens. J. Nucl. Med. 47:196-199.
24. Jain M, Venkatraman G, Batra S K (2007) Optimization of radioimmunotherapy of solid tumors: Biological impediments and their modulation. Clin. Cancer Res. 13:1374-1382.
25. Brans B, Linden O, Giammarile F, Tennvall J, Punt C (2006) Clinical applications of newer radionuclide therapies. Eur. J. Cancer 42:994-1003.
26. Bertagnolli M (2005) Radioimmunotherapy for colorectal cancer. Clin. Cancer Res. 11:4337-4338.
27. Zafir-Lavie I, Michaeli Y, Reiter Y (2007) Novel antibodies as anticancer agents. Oncogene 26: 3714-3733.

The invention claimed is:

1. A method of delivering a radioactive isotope to a colon adenocarcinoma cell, comprising:
   administering to a colon adenocarcinoma cell a radioactive isotope-labeled peptide, wherein the peptide is a substrate for protein kinase A (PKA) comprising the sequence of SEQ ID NO: 5.

2. The method of claim 1 wherein the radioactive isotope is $^{32}P$ or $^{33}P$.

3. The method of claim 1 wherein the radioactive isotope is $^{125}I$ or $^{131}I$.

4. The method of claim 1 wherein the adenocarcinoma cell is in a patient with a colon tumor.

5. The method of claim 1 further comprising the step of: determining location of the radioactive isotope in the patient by an imaging technique.

6. The method of claim 1 further comprising the step of: monitoring size of the tumor.

7. The method of claim 1 wherein the adenocarcinoma cell is in a xenograft in an animal.

8. The method of claim 1 wherein the adenocarcinoma cell is in culture.

* * * * *

UNITED STATES PATENT AND TRADEMARK OFFICE
CERTIFICATE OF CORRECTION

PATENT NO. : 8,435,490 B2  Page 1 of 1
APPLICATION NO. : 12/664302
DATED : May 7, 2013
INVENTOR(S) : Abraham et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 454 days.

Signed and Sealed this
Eighth Day of September, 2015

Michelle K. Lee
*Director of the United States Patent and Trademark Office*